United States Patent [19]

Payard et al.

[11] Patent Number: 5,519,023
[45] Date of Patent: May 21, 1996

[54] AMINOALKYLCHROMONES, PROCESSES FOR THE PREPARATION THEREOF

[75] Inventors: Marc Payard, Balma; Geneviève Baziard-Mouysset; Gilbert De Saqui-Sannes, both of Toulouse; Béatrice Guardiola, Neuilly; Daniel-Henri Caignard, Paris; Pierre Renard, Versailles; Gérard Adam, Le Mesnil le Roi, all of France

[73] Assignee: Adir et Compagnie, Courbevoie, France

[21] Appl. No.: 94,564

[22] Filed: Jul. 2, 1993

[30] Foreign Application Priority Data

Jul. 21, 1992 [FR] France .................... 92 08950

[51] Int. Cl.$^6$ .............. A61K 31/495; A61K 31/445; C07D 405/14; C07D 405/06
[52] U.S. Cl. .............. 514/253; 514/218; 514/228.2; 514/278; 514/320; 514/397; 514/402; 514/414; 514/422; 540/450; 540/575; 540/596; 544/62; 544/295; 544/364; 544/376; 544/377; 544/399; 546/16; 546/196; 548/311.4; 548/454; 548/525
[58] Field of Search ................... 544/376, 377, 544/295, 62, 376, 377; 548/311.4, 525; 540/575; 546/196; 514/253, 397, 422, 402, 218, 320, 228.2

[56] References Cited

U.S. PATENT DOCUMENTS

| 3,767,679 | 10/1973 | von Strandtmann | 544/376 |
| 4,092,416 | 5/1978 | Winter et al. | 544/376 |
| 5,278,174 | 1/1994 | Erickson et al. | 514/320 |
| 5,364,867 | 11/1994 | DeHaven-Hudkins | 514/326 |

OTHER PUBLICATIONS

Weiner et al., *The sigma ligand BMY-14802 as a potential antipsychotic: evidence from the latent inhibition model in rats*, Behavioral Pharmacology 6, 46–54 (1995).

Sanchez et al., *A Selective Sigma Ligand With Potent Anxiolytic Effects*, in Society for Neuroscience Abstracts, vol. 20, Part 1, 385 (1994).

Leonard, *The enigma of sigma receptors*, in Abstracts of the VIIth Congress of the European College of Neuropsychopharmacology, vol. 4, No. 3, 174–175 (1994).

Okuyama et al., *NE–100, A Novel Sigma Receptor Ligand: Effect on Phencyclidine–Induced Behaviors in Rats, Dogs and Monkeys*, Life Sciences, vol. 55, No. 7, PL 133–138 (1994).

Moore, Biological Psychiatry 12, No. 3, 451–462 (1977).

Animal Models and Psychiatry, H. Verdoux, M. Bourgeois, Monographs of the ANPP, vol. 5, cover and p. 25 with English Translation of the pertinent part (1991).

Butcher et al., J. Neurochemistry 50, No. 2, 346–355 (1988).

Gewirtz et al, *Neuropsychopharmacology* 10, pp. 37–40 (1994).

Primary Examiner—Emily Bernhardt
Attorney, Agent, or Firm—The Firm of Gordon W. Hueschen

[57] ABSTRACT

The invention relates to compounds of the general formula (I):

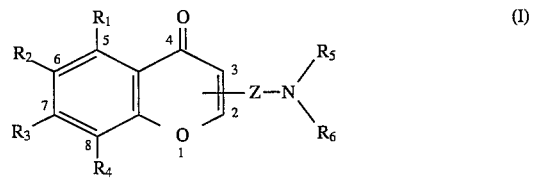

wherein $R_1$, $R_2$, $R_3$, $R_4$, $R_5$, $R_6$ and Z are as defined in the description, their optical isomers and their addition salts with a pharmaceutically-acceptable acid or base and medicaments containing the same, useful in the treatment and prevention of stress, anxiety, and related ailments.

14 Claims, No Drawings

AMINOALKYLCHROMONES, PROCESSES FOR THE PREPARATION THEREOF

The present invention relates to new aminoalkylchromones, processes for the preparation thereof and pharmaceutical compositions containing them.

Some aminoalkylchromones are already known (U.S. Pat. No. 3,767,679) for their activity in the prevention of allergic symptoms.

The Applicants have now discovered new aminoalkylchromones possessing remarkable pharmacological properties.

In particular, the compounds of the invention have been found to be powerful ligands of sigma ($\sigma$) receptors and as such can be used in disorders of the central nervous system, which distinguishes them completely from the compounds of the prior art.

More especially, the present invention relates to the compounds of formula (I):

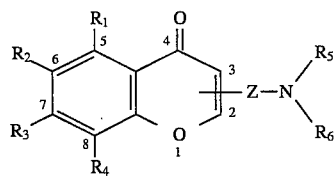

in which:

Z represents a methylene chain optionally substituted by a lower acyl radical, each of $R_1$, $R_2$, $R_3$ and $R_4$, independently of the others, represents a radical selected from:

hydrogen, halogen, hydroxy, lower alkoxy, lower alkyl, phenyl, benzyl, and trifluoromethyl, $R_5$ and $R_6$: either form together, with the nitrogen atom carrying them, a heterocycle selected from:

unsubstituted and substituted pyrrole, unsubstituted and substituted imidazole, unsubstituted and substituted imidazolidine, unsubstituted and substituted piperazine, unsubstituted and substituted homopiperazine, substituted piperidine, thiomorpholine, unsubstituted and substituted azaspirane having from 8 to 12 ring members, and unsubstituted and substituted azacycloalkyl, or $R_5$ represents a radical —$(CH_2)_n$—A, n representing an integer from 1 to 4 inclusive and A being a radical selected from:

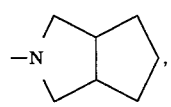, 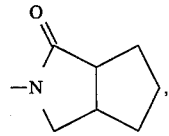,

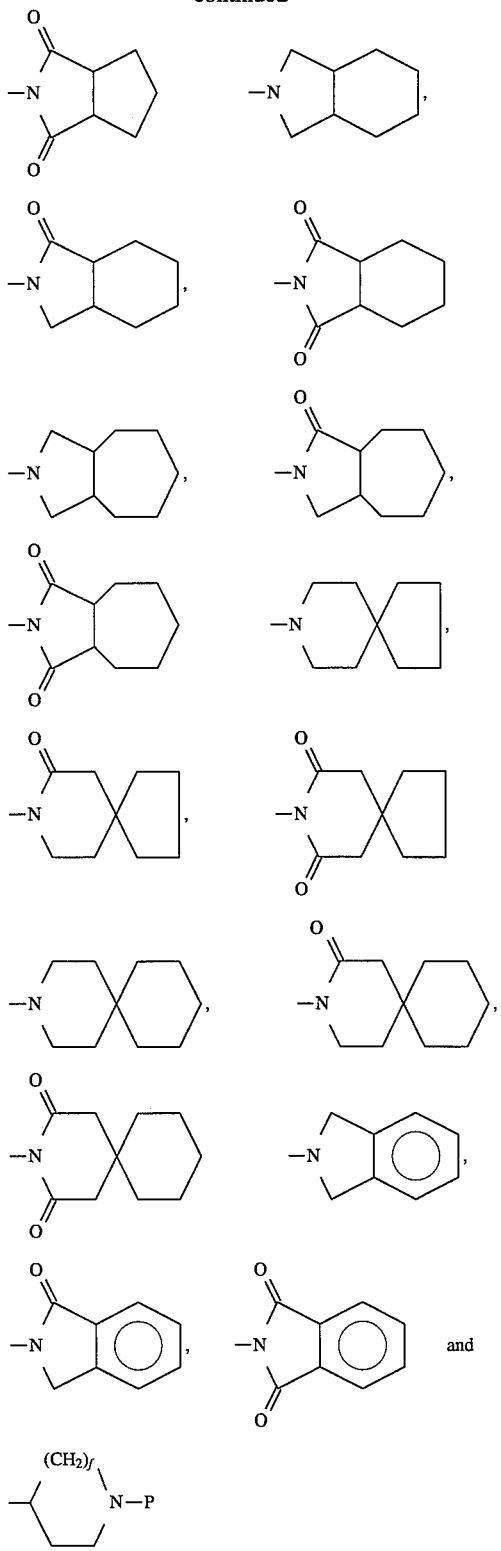

in which f represents an integer from 1 to 3 inclusive and P represents a grouping:

lower alkyl, phenyl that is unsubstituted or substituted by one or more radicals selected from halogen, trifluoromethyl, linear and branched alkyl having from 1 to 4 carbon atoms, and linear and branched alkoxy having from 1 to 4 carbon atoms, napthnyl that is unsubstituted or substituted by one or more radicals selected from halogen, trifluoromethyl, linear and branched alkyl having from 1 to 4 carbon atoms, and linear and branched alkoxy having from 1 to 4 carbon atoms, phenyl-lower alkyl that is unsubstituted or substituted by one or more radicals selected from halogen, trifluoromethyl, linear and branched alkyl having from 1 to 4 carbon atoms, and linear and branched alkoxy having from 1 to 4 carbon atoms, or naphthyl-lower alkyl that is unsubstituted or substituted by one or more radicals selected from halogen, trifluoromethyl, linear and branched alkyl having from 1 to 4 carbon atoms, and linear and branched alkoxy having from 1 to 4 carbon atoms, and $R_6$ represents a radical selected from hydrogen, lower alkyl, lower alkenyl and $—(CH_2)_{n'}—A'$ in which n' and A' have the same meanings as n and A, respectively, defined above, it being understood that, unless otherwise indicated:

the term "unsubstituted and substituted azacycloalkyl" denotes a mono- or bi-cyclic hydrocarbon skeleton having from 8 to 15 ring members, including a nitrogen atom and optionally one or two additional hetero atoms selected from oxygen, nitrogen and sulfur, this azacycloalkyl being unsubstituted or substituted by one or more radicals selected from:

halogen, hydroxy, amino, oxo, mercapto, linear and branched alkyl having from i to 4 carbon atoms, and linear and branched alkoxy having from 1 to 4 carbon atoms, the terms "lower alkyl", "lower alkoxy" and "lower acyl" denote linear or branched groupings containing from 1 to 6 carbon atoms, the term "lower alkenyl" denotes a linear or branched unsaturated radical containing from 2 to 8 carbon atoms, the term "substituted" associated with a piperidine grouping denotes that that grouping is substituted by a phenyl, naphthyl, phenyl-lower alkyl or naphthyl-lower alkyl radical optionally substituted on the phenyl and naphthyl groups by one or more radicals selected from:

halogen, hydroxy, mercapto, trifluoromethyl, lower alkyl, lower alkoxy, and lower alkoxycarbonyl, the term "substituted" associated with pyrrole, imidazole, imidazolidine, piperazine, homopiperazine and azaspirane radicals denotes that those radicals are substituted by one or more radicals selected from:

oxo,

—$R_9$,

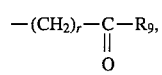

in which r is 0 or an integer from 1 to 4, and $R_9$ represents a diphenyl-lower alkyl radical that is unsubstituted or substituted on at least one of the phenyl rings by one or more radicals selected from halogen, hydroxy, linear and branched alkyl having from 1 to 4 carbon atoms, linear and branched alkoxy having from 1 to 4 carbon atoms, and trifluoromethyl, a (dicyclopropyl)-lower alkyl radical that is unsubstituted or substituted on at least one of the rings by one or more radicals selected from halogen, hydroxy, linear and branched alkyl having from 1 to 4 carbon atoms, and linear and branched alkoxy having from 1 to 4 carbon atoms, an unsubstituted or substituted $—(CH_2)_p$-phenyl radical in which p is an integer from 1 to 5 inclusive, an unsubstituted or substituted $—(CH_2)_q$-naphthyl radical in which q is 0 or an integer from 1 to 5 inclusive, a radical $—R_{10}$ that is unsubstituted or substituted by one or more radicals selected from halogen and hydroxy, $R_{10}$ representing a lower alkyl, lower alkoxy or lower alkenyl radical, or a radical $—(CH_2)_t—R_{11}$ in which t is 0 or an integer from 1 to 5 inclusive, and $R_{11}$ represents a radical selected from: pyrazinyl, pyrimidinyl, thienyl, pyrrolyl, furyl, thiazolyl, benzothiazolyl, pyridyl, quinolyl, isoquinolyl, benzofuryl, benzothienyl, indolyl, cycloalkyl having from 3 to 8 ring members that is optionally fused to a benzene ring, heterocycloalkyl having from 5 to 10 ring members that includes in its carbon skeleton a hetero atom selected from oxygen, nitrogen and sulfur and is optionally fused to a benzene ring, (1,3-benzodioxol-5 -yl)-lower alkyl, and (1,4-benzoxan-6-yl)-lower alkyl, the term "substituted" associated with the "$—(CH_2)_p$-phenyl" radical denotes that that radical is substituted on the phenyl ring by 1, 2, 3 or 4 radicals selected from:

halogen, hydroxy, mercapto, and unsubstituted $R_{12}$ and $R_{12}$ substituted by one or more radicals selected from halogen and hydroxy, $R_{12}$ representing a lower alkyl or lower alkoxy radical, the term "substituted" associated with the "$—(CH_2)_q$-naphthyl" radical denotes that the naphthyl ring is substituted by one or more radicals selected from:

halogen, hydroxy, mercapto, and unsubstituted $R_{12}$ and $R_{12}$ substituted by one or more radicals selected from halogen and hydroxy, $R_{12}$ being as defined above, their optical isomers, and also their addition salts with a pharmaceutically acceptable acid or base.

Of the acids used for the formation of the addition salts of the compounds of formula (I) there may be mentioned by way of non-limiting examples, from the mineral series, hydrochloric, hydrobromic, sulfuric and phosphoric acid, and, from the organic series, acetic, propionic, maleic, fumaric, tartaric, citric, oxalic, benzoic and methanesulfonic acid.

Of the bases used for the formation of the addition salts of the compounds of formula (I) there may be mentioned by way of non-limiting examples, from the mineral series, sodium, potassium, calcium and aluminium hydroxide, and alkaline earth metal carbonates, and from the organic series, triethylamine, benzylamine, diethylamine, tert-butylamine, dicyclohexylamine and arginine.

The present invention extends also to a process for the preparation of the compounds of formula (I), characterised in that an amine of formula (II):

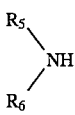
(II)

in which $R_5$ and $R_6$ are as defined in formula (I), is reacted with a haloalkylchromone compound of formula (III):

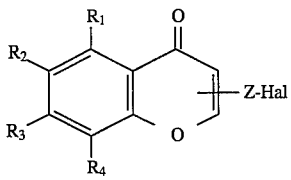
(III)

in which $R_1$, $R_2$, $R_3$, $R_4$ and Z are as defined in formula (I) and Hal represents a halogen atom, in order to obtain the compounds of formula (I), which compounds of formula (I) may, if desired, be purified in accordance with one or more purification methods selected from crystallisation, chromatography on silica gel, extraction, filtration, and passage over activated charcoal and/or resin, separated, where appropriate, in pure form or in the form of a mixture, into their possible optical isomers, and/or converted into a salt using a pharmaceutically acceptable acid or base.

The present invention extends also to a process for the preparation of the compounds of formula (I/A):

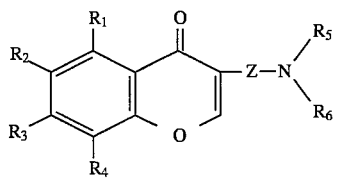
(I/A)

in which $R_1$, $R_2$, $R_3$, $R_4$, $R_5$, $R_6$ and Z are as defined in formula (I), which is a particular case of the compounds of formula (I) in which the chromone is substituted in the 2-position by the radical

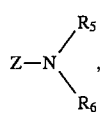

characterised in that an amine of formula (II):

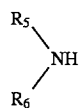
(II)

in which $R_5$ and $R_6$ are as defined in formula (I), is reacted with a compound of formula (IV):

Hal'—Z—COO—CH$_2$CH$_3$ (IV)

in which Z is as defined above and Hal' represents a halogen atom, in order to obtain a compound of formula (V):

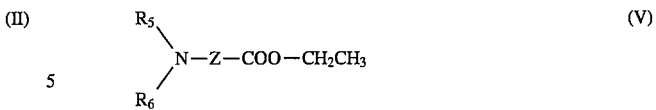
(V)

in which $R_5$, $R_6$ and Z are as defined above, which compound of formula (V) is reacted with an orthohydroxyacetophenone compound of formula (VI):

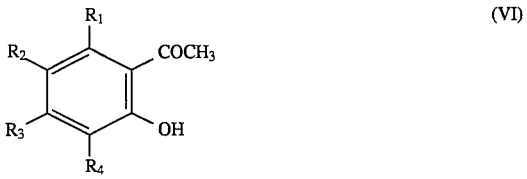
(VI)

in which $R_1$, $R_2$, $R_3$ and $R_4$ are as defined in formula (I), in order to obtain the compounds of formula (I/A) such as defined above, which compounds of formula (I/A) may, if desired, be purified in accordance with one or more purification methods selected from crystallisation, chromatography on silica gel, extraction, filtration, and passage over activated charcoal and/or resin, separated, where appropriate, in pure form or in the form of a mixture, into their possible optical isomers, and/or converted into a salt using a pharmaceutically acceptable acid or base.

The starting materials used in the processes described above are:

either commercial, or readily accessible to the person skilled in the art in accordance with processes described in the literature.

The Applicants have discovered that the compounds of the invention possess very valuable pharmacological properties.

σ (sigma) receptor-binding tests have demonstrated that the compounds of the invention act as very powerful ligands of those receptors ("Measurement of the affinity of the compounds of the invention for σ (sigma) receptors": Example B of the present Application).

In addition, the Applicants have discovered that the compounds of formula (I) exhibit a very good selectivity with respect to σ (sigma) receptors, especially compared with dopaminergic $D_2$ receptors ("Measurement of the affinity of the compounds of the invention for $\beta_1$, $\beta_2$, $D_1$, $D_2$, $5HT_{1A}$, $5HT_{1C}$, $5HT_{1D}$, $5HT_2$ and $5HT_3$": Example C of the present Application).

This selectivity confers on them remarkable pure neuroleptic, antipsychotic and psychotogenic properties ("Study of the antagonism of hyperactivity induced by d-amphetamine sulfate in mice": Example D of the present Application and "Study of the antagonism of behavioural stereotypes induced in rats by phencyclidine": Example E of the present Application), which properties have no secondary effects attributable to the extra-pyramidal component currently associated with neuroleptics ("Study of the reversal of the effects of apomorphine in rats": Example F of the present Application).

The compounds of the present invention can thus be used in the treatment and prevention of stress, anxiety, depression, psychoses and schizophrenia, without having to contend with the usual secondary effects of the Parkinsonian type, including akinesia, trembling, and rigidity of the limbs, associated with neuroleptics of the conventional type.

The present invention relates also to pharmaceutical compositions comprising a compound of the general formula (I), or one of its physiologically tolerable salts, in combination with one or more pharmaceutically acceptable excipients or carriers.

Of the pharmaceutical compositions according to the invention there may be mentioned by way of non-limiting examples those that are suitable for oral, nasal or parenteral administration, and especially tablets, dragées, gelatin capsules, packets, sachets, granules, pills, granulates, suppositories, creams, ointments, aerosols, capsules, dermal gels and injectable or drinkable solutions.

The dosage varies from individual to individual according to the age, weight and sex of the patient, the mode of administration selected and the nature and severity of the disorder. The doses used range from 0.1 to 100 mg per treatment, divisible into 1 to 3 doses per 24 hours.

The following Examples illustrate the invention and do not limit it in any way.

EXAMPLE 1

2-[(4-Benzylpiperazin-1-yl)Methyl]-4-Oxo[4H]-1-Benzopyran

First Synthesis Process 0.02 mol of 2-chloromethyl-4-oxo[4H]-1-benzopyran is dissolved in 200 cm$^3$ of tetrahydrofuran. 0.04 mol of 1-benzylpiperazine is then added. The progress of the reaction is followed by thin layer chromatography.

When all of the chloro compound has reacted, the solvent is evaporated off under reduced pressure. The residue is taken up in ether. The solution is filtered, evaporated and chromatographed on a silica gel column using 1,2-dichloroethane as eluant. 2-[(4-benzylpiperazin-1-yl)methyl]-4-oxo[4H]-1-benzopyran is obtained.

Melting point (base): oil

Melting point (dihydrochloride): 238° C.

Yield (dihydrochloride): 79%

Spectral characteristics (base):
Infra-red:

$\upsilon$C-H, CH$_2$: 2815, 2879, 2913, 2937, 3026, 3061, 3083 cm$^{-1}$ $\upsilon$C=O: 1654 cm$^{-1}$ $\upsilon$C=C: 1463, 1570, 1607 cm$^{-1}$ NMR (CDCl$_3$)
$\delta$(ppm)
2.63 m 8H CH$_2$-N
3.48 s 2H Ar-CH$_2$-N
3.52 s 2H Ar-CH$_2$-N
6.43 s 1H H$_3$
7.27–7.77 m 8H aromatic
8.2 dd 1H H$_5$

EXAMPLE 2

2-[(4-Benzylpiperazin-1-yl)Methyl]-4-Oxo[4H]-1-Benzopyran

Second Synthesis Process

Stage A: ethyl 2-(4-benzylpiperazin-1-yl)acetate 21 g (0.12 mol) of 1-benzylpiperazine, 13.4 cm$^3$ or 20 g (0.12 mol) of ethyl bromoacetate and 200 cm$^3$ of ethanol are introduced into a 500 cm$^3$ Erlenmeyer flask. The mixture is heated under reflux for 30 minutes. 17 g (0.12 mol) of potassium carbonate are then added and refluxing is continued for a further one hour. After cooling, the mixture is filtered and the filtrate is evaporated under reduced pressure. The residue is taken up in a mixture of 200 cm$^3$ of water and 200 cm$^3$ of chloroform. After extraction, the organic phase is dried, filtered and evaporated.

29 g of ethyl 2-(4-benzylpiperazin-1-yl)acetate are thus obtained in the form of a crude brown oil.

The oil is purified by distillation under reduced pressure. 22.5 g of a colourless viscous oil are thus obtained.

Melting point (base): oil

Yield (base): 72%

Spectral characteristics (base):

Infra-red:

$\upsilon$ CH, CH$_2$: 2811, 2934, 2979, 3025 cm$^{-1}$ $\upsilon$COO: 1747 cm$^{-1}$ $\upsilon$C=C: 1451, 1676 cm$^{-1}$ NMR (CDCl$_3$)
$\delta$(ppm)
1.2 t 3H CH$_3$
2.56 m 8H CH$_2$
3.13 s 2H CH$_2$-CO
3.46 s 2H CH$_2$ aromatic
4.13 q 2H CH$_2$O
7.2 m 5H aromatic Stage B: 2-[(4-benzylpiperazin-1-yl)methyl]-4-oxo[4H]-1-benzopyran 100 cm$^3$ of anhydrous pyridine, 13 g (0.05 mol) of the compound obtained in stage A and 7.5 g (0,055 mol) of 2-hydroxyacetophenone are introduced into a 500 cm$^3$ Erlenmeyer flask. 10 g (0.41 mol) of sodium hydride dispersed in mineral oil (60%) are then added very slowly in small portions, with stirring. When the evolution of gas has ceased, the mixture is heated to reflux temperature and stirred for 45 minutes. After cooling, filtration is carried out. The precipitate obtained is washed with ether and then added in small portions to 50 cm$^3$ of concentrated hydrochloric acid and cooled externally with ice. The reaction is violent. When the addition is complete, heating under reflux is carried out for 5 minutes. After cooling, 200 cm$^3$ of water are added and extraction is carried out with 2×100 cm$^3$ of chloroform.

The aqueous phase is rendered alkaline to pH 9 with potassium carbonate and extracted again with 2×100 cm$^3$ of chloroform. This last organic phase is dried, filtered and evaporated. The oil obtained is purified by chromatography on silica gel using methyl chloroform as eluant.

6 g of 2-[(4-benzylpiperazin-1-yl)methyl]-4-oxo[4H]-1-benzopyran are thus recovered.

Melting point (base): oil

Melting point (dihydrochloride): 238° C.

Spectral characteristics (base):
Infra-red:

$\upsilon$CH, CH$_2$: 2815, 2879, 2913, 2937, 3026, 3061, 3083 cm$^{-1}$ $\upsilon$C=O: 1654 cm$^1$ $\upsilon$C=C: 1463, 1570, 1607 cm$^{-1}$ NMR (CDCl$_3$)
$\delta$(ppm)
2.63 m 8H CH$_2$-N
3.48 s 2H Aromatic-CH$_2$-N
3.52 s 2H Aromatic-CH$_2$-N
6.43 s 1H H$_3$
7.27–7.77 m 8H aromatic
8.2 dd 1H H$_5$

EXAMPLE 3

2-[(4-Benzylpiperazin-1-yl)Methyl]-5-Chloro-4-Oxo[4H]-1-Benzopyran

By proceeding as in Example 2, but replacing the 2-hydroxyacetophenone in stage B by 2-hydroxy-6-chloroacetophenone, the title compound is obtained.

EXAMPLE 4

2-[1-(4-Benzylpiperazin-1-yl)-1-Acetylmethyl]-4-Oxo[4H]-1-Benzopyran

By proceeding as in Example 2, but replacing the ethyl bromoacetate in stage A by ethyl 2-chloro-2-acetoacetate, the title compound is obtained.

EXAMPLES 5 to 7

By proceeding as in Examples 2, and 4, but replacing the 1-benzylpiperazine in stage A by 1-{1-[di(cyclopropyl)]methyl}piperazine, the following compounds, respectively, are obtained:

EXAMPLE 5

2-{[4-[1-(Dicyclopropyl)Methyl]Piperazin-1-yl]Methyl}-4-Oxo[ 4H]-1-Benzopyran

EXAMPLE 6

2-{[4-[1-(Dicyclopropyl)Methyl]Piperazin-1-yl]Methyl}-5-Chloro-4-Oxo[4H]-1-Benzopyran

EXAMPLE 7

2-{1-[4-[1-(Dicyclopropyl)Methyl]Piperazin-1-yl]-1-Acetylmethyl}-4-Oxo[4H]-1-Benzopyran

EXAMPLE 8

2-{[4-(3,5-Diisopropyl-4-Hydroxybenzyl)Piperazin-1-yl]methyl}-4-Oxo[4H]-1-Benzopyran By proceeding as in Example 2, but replacing the 1-benzylpiperazine in stage A by 1-(3,5-diisopropyl-4-hydroxybenzyl)piperazine, the title compound is obtained.

EXAMPLE 9

2-{[4-(2,5-Dimethoxybenzyl)Piperazin-1-yl]methyl}-4-Oxo[4H]-1-Benzopyran

By proceeding as in Example 2, but replacing the 1-benzylpiperazine in stage A by 1-(2,5-dimethoxybenzyl)piperazine, the title compound is obtained.

EXAMPLE 10

2-{4-(3,4-Dimethylbenzyl)Piperazin-1-yl]Methyl}-4-Oxo[4H]-1-Benzopyran

By proceeding as in Example 2, but replacing the 1-benzylpiperazine in stage A by 1-(3,4-dimethylbenzyl)piperazine, the title compound is obtained.

EXAMPLES 11 to 18

By proceeding as in Example 2, but replacing the 1-benzylpiperazine in stage A by appropriately substituted 1-benzylpiperazine compounds, the following compounds are obtained:

EXAMPLE 11

2-{[4-(2,4-Dimethoxybenzyl)Piperazin-1-yl]Methyl}-4-Oxo[4H]-1-Benzopyran

EXAMPLE 12

2-{[4-(2,4-Ditrifluoromethylbenzyl)Piperazin-1-yl]Methyl}-4Oxo[ 4H]-1-Benzopyran

EXAMPLE 13

2-{[4-(2,4-Dichlorobenzyl)Piperazin-1-yl]methyl}-4-Oxo[4H]-1-Benzopyran

Melting point (base): 93° C.
Melting point (dihydrochloride): 198° C.
Yield (base): 50%
Yield (dihydrochloride): 84%

EXAMPLE 14

2-{[4-(3,4-Dichlorobenzyl)Piperazin-1-yl]Methyl}-4-Oxo[4H]-1-Benzopyran

Melting point (base): 136° C.
Melting point (dihydrochloride): 222° C.
Yield (base): 37%
Yield (dihydrochloride): 88%

EXAMPLE 15

2-{[4-(3,5-Di(Tert-Butyl)-4-Hydroxybenzyl)Piperazin-1-yl] methyl}-4-Oxo[4H]-1-Benzopyran

EXAMPLE 16

2-{[4-(2,3,4-Trimethylbenzyl)Piperazin-1-yl]Methyl}-4Oxo[ 4H]-1-Benzopyran

Melting point (base): oil
Melting point (dihydrochloride): 181° C.
Yield (base): 54%

EXAMPLE 17

2-{[4-(2,4,6-Trimethylbenzyl)Piperazin-1N-1-yl]Methyl}-4-Oxo [4H]-1-Benzopyran

EXAMPLE 18

2-{[4-(3,4,5-Trimethylbenzyl)Piperazin-1-yl]Methyl}-4-Oxo [4H]-1-Benzopyran

EXAMPLE 19

2-{4-(2,4-Dichlorophenethyl)Piperazin-1-yl)]Methyl}-4-Oxo[4H]- 1-Benzopyran

By proceeding as in Example 2, but replacing the 1-benzylpiperazine in stage A by 1-[2,4-dichloro(phenethyl)] piperazine, the title compound is obtained.

EXAMPLE 20

2-[(Pyrrolidin-1-yl)Methyl]-4-Oxo[4H]-1-Benzopyran

By proceeding as in Example 2, but replacing the 1-benzylpiperazine in stage A by pyrrolidine, the title compound is obtained.

EXAMPLE 21

2-[(Perhydroazepin-1-yl)Methyl]-4-Oxo[4H]-1-Benzopyran

By proceeding as in Example 2, but replacing the 1-benzylpiperazine in stage A by perhydroazepine, the title compound is obtained.

EXAMPLE 22

2-[(4-Benzhydrylpiperazin-1-yl)methyl]-4-Oxo[4H]-1-Benzopyran

By proceeding as in Example 2, but replacing the 1-benzylpiperazine in stage A by 1-benzhydrylpiperazine, the title compound is obtained.

Melting point (base): 68° C.
Melting point (dihydrochloride): 234° C.
Yield (dihydrochloride): 91%

EXAMPLE 23

2-{[4-[1-(4'-Chlorophenyl)-1-(Phenyl)Methyl]Piperazin-1-yl]Methyl}-4-Oxo[4H]-1-Benzopyran By proceeding as in Example 2, but replacing the 1-benzylpiperazine in stage A by 1-{[1-(4'-chlorophenyl)-1-Phenyl] methyl}piperazine, the title product is obtained in the same manner.

EXAMPLES 24 to 35

By proceeding as in Example 2, but replacing the 1-benzylpiperazine in stage A by appropriately substituted piperazines, the following Examples are obtained:

EXAMPLE 24

2-{[4-[(1,3-Benzodioxol-5-yl)Methyl]Piperazin-1-yl]methyl}-4-Oxo[4H]-1-Benzopyran Melting point (base): 114°–118° C.
Melting point (dihydrochloride): 124° C.
Yield (base): 59%

EXAMPLE 25

2-{[4-[2-(1,3-Benzodioxol-5-yl)Ethyl]Piperazin-1-yl]Methyl}-4-Oxo[4H]-1-Benzopyran

EXAMPLE 26

2-{[4-(Pyrimidin-2-yl)Piperazin-1-yl]methyl}-4-Oxo[4H]-1-Benzopyran

Melting point (base): 169° C.
Melting point (dihydrochloride): 198° C.

EXAMPLE 27

2-{[4-(Pyrid-2-yl)Piperazin-1-yl]Methyl}-4-Oxo[4H]-1-Benzopyran

EXAMPLE 28

2-[(4-Methylpiperazin-1-yl)Methyl]-4-Oxo[4H]-1-Benzopyran

Melting point (dihydrochloride): 222° C.

EXAMPLE 29

2-{[4-[(Pyrrolidin-1-yl)Carbonylmethyl]Piperazin-1-yl]methyl}-4-Oxo [4H]-1-Benzopyran

EXAMPLE 30

2-[(4-Ethoxycarbonylpiperazin-1-yl)Methyl]-4-Oxo[4H]-1-Benzopyran

EXAMPLE 31

2-[(2,5-Dimethylpiperazin-1-yl)Methyl]-4-Oxo[4H]-1-Benzopyran

EXAMPLE 32

2-{[4-(Propen-2-yl)Piperazin-1-yl]Methyl}-4-Oxo[4H]-1-Benzopyran

EXAMPLE 33

2-{[4-(Naphth-2-yl)Piperazin-1-yl]Methyl}-4-Oxo[4H]-1-Benzopyran

EXAMPLE 34

2-{[4-(2,4-Dichlorophenylacetylmethyl)Piperazin-1-yl]Methyl}-4-Oxo[4H]-1-Benzopyran

EXAMPLE 35

2-{[4-(Pyrrolylmethylcarbonylmethyl)Piperazin-1-yl]Methyl}-4-Oxo [4H]-1-Benzopyran

EXAMPLES 36 to 48

By proceeding as in Example 2, but replacing the 1-benzylpiperazine in stage A by appropriate amines, the following Examples are obtained:

EXAMPLE 36

2-(Azacyclooctylmethyl)-4-Oxo[4H]-1-Benzopyran

Melting point (base): oil
Melting point (hydrochloride): 157° C.
Yield (base): 55%
Yield (hydrochloride): 65%

EXAMPLE 37

2-(Imidazol-1-ylmethyl)-4-Oxo[4H]-1-Benzopyran

Melting point (base): 163° C.
Melting point (hydrochloride): 201° C.
Yield (base): 52%

EXAMPLE 38

2-(Thiomorpholin-4-ylmethyl)-4-Oxo[4H]-1-Benzopyran

EXAMPLE 39

2-[(7-Oxo-8-Azaspiro[5.4]Dec-8-yl)Methyl]-4-Oxo[4H]-1-Benzopyran

EXAMPLE 40

2-[(2,4-Dioxo-3-Azaspiro[5.5]Undec-3-yl)methyl]-4-Oxo[4H]-1-Benzopyran

EXAMPLE 41

2-[(8-Azabicyclo[4.3.0]Non-8-yl)Methyl]-4-Oxo[4H]-1-Benzopyran

EXAMPLE 42

2-{[4-(2-Naphth-2-ylethyl)Piperidin-1-yl]Methyl}-4-Oxo[4H]-1-Benzopyran

EXAMPLE 43

2-[(4-Phenylpiperidin-1-yl)Methyl]-4-Oxo[4H]-1-Benzopyran

EXAMPLE 44

2-[(4-Benzylpiperidin-1-yl)Methyl]-4-Oxo[4H]-1-Benzopyran

Melting point (base): oil
Melting point (hydrochloride): 208° C.
Yield (base): 10%
Yield (hydrochloride): 90%

EXAMPLE 45

2-{[N-Propyl-N-[(1-Benzylpiperidin-4-yl)Methyl]Amino]Methyl}- 4-Oxo[4H]-1-Benzopyran

EXAMPLE 46

2-{[N-Methyl-N-[4-(7,9-Dioxo-8-Azaspiro[4.5]DEC-8-yl)Butyl] Amino]methyl}-4-Oxo[4H]-1-Benzopyran

EXAMPLE 47

2-{[N-methyl-N-[4-(1,3-Dioxoazabicyclo[3.3.0]Oct-2-yl)Butyl] Amino]Methyl}-4-Oxo[4H]-1-Benzopyran

EXAMPLE 48

2-{[N-Ethyl-N-(Phthalimidoethyl)Amino]Methyl}-4-Oxo[4H]-1-Benzopyran

EXAMPLE 49

2-[(7,9-Dioxo-8-Azaspiro[4.5]Dec-8-yl)Methyl]-4-Oxo[4H]-1-Benzopyran

EXAMPLES 50 to 52

By proceeding as in Example 2, but replacing the 1-benzylpiperazine in stage A by appropriate amines and replacing the 2-hydroxyacetophenone in stage B by appropriately substituted 2-hydroxyacetophenone compounds, the following compounds are obtained:

EXAMPLE 50

2-(Thiomorpholin-4-ylmethyl)-8-Methoxy-4-Oxo[4H]-1-Benzopyran

EXAMPLE 51

2-[(7,9-Dioxo-8-Azaspiro[4.5]Dec-8-yl)methyl]-4-Oxo-7-Trifluoromethyl [4H]-1-Benzopyran

EXAMPLE 52

2-[(8-Azabicyclo[4.3.0]Non-8-yl)Methyl]-7-Chloro-4-Oxo[4H]-1-Benzopyran

EXAMPLE 53

2-[(8-Azabicyclo[4.3.0]Non-8-yl)-1-Acetylmethyl]-7-Chloro-4-Oxo [4H]-1-Benzopyran By proceeding as in Example 52, but replacing the ethyl bromoacetate in stage A by ethyl 2-chloro-2-acetoacetate, the title compound is obtained.

EXAMPLE 54

3-[(4-Benzylpiperazin-1-yl)Methyl]-4-Oxo[4H]-1-Benzopyran 0.02 mol of 3-chloromethyl-4-oxo[4H]-1-benzofuran is dissolved in 200 cm$^3$ of tetrahydrofuran. 0.04 mol of 1-benzylpiperazine is then added. The progress of the reaction is followed by thin layer chromatography. When all of the chloro compound has reacted, the solvent is evaporated off under reduced pressure. The residue is taken up in ether. The solution is filtered, evaporated and chromatographed on a silica gel column using 1,2-dichloroethane as eluant. 3-[(4-benzylpiperazin-1-yl) methyl]-4-oxo[4H]-1-benzopyran is obtained.

EXAMPLES 55 to 60

By proceeding as in Example 54, but replacing the 1-benzylpiperazine by the appropriate amine compounds, the following compounds are obtained:

EXAMPLE 55

3-{[4-(2,3,4-Trimethylbenzyl)Piperazin-1-yl]Methyl}-4-Oxo [4H]-1-Benzopyran

EXAMPLE 56

3-([4-(3,4-Dichlorobenzyl)Piperazin-1-yl)Methyl}-4-Oxo[4H]-1-Benzopyran

EXAMPLE 57

3-([4-(2,4-Dichlorobenzyl)Piperazin-1-yl)Methyl}-4-Oxo[4H]-1-Benzopyran

EXAMPLE 58

3-[(4-Naphth-2-ylpiperazin-1-yl)Methyl]-4-Oxo [4H]-1-Benzopyran

EXAMPLE 59

3-{[4-[(1,3-Benzodioxol-5-yl)methyl]Piperazin-1-yl]Methyl}-4-Oxo[ 4H]-1-Benzopyran

EXAMPLE 60

3-([[N-Ethyl-N-(2-Phthalimidoethyl)]Amino]methyl}-4-Oxo[4H]-1-Benzopyran

EXAMPLE 61

2-[4-(4-Methoxybezyl)Piperazin-1-ylmethyl]-4-Oxo [4H]-1-Benzopyran

By proceeding as in Example 2, but replacing the 1-benzylpiperazine in stage A by the 1-(4-methoxybenzyl)piperazine, the title compound is obtained.

Melting point (base): 101° C.
Melting point (dihydrochloride): 226° C.
Yield (base): 43%
Yield (dihydrochloride): 97%

EXAMPLE 62

2-[4-(4-Fluorobenzyl)Piperazin-1-ylmethyl]-4-Oxo [4H]-1-Benzopyran

By proceeding as in Example 2, but replacing the 1-benzylpiperazine in stage A by the 1-(4-fluorobenzyl)piperazine, the title compound is obtained.

Melting point (base): 106° C.
Melting point (dihydrochloride): 221° C.
Yield (base): 57%
Yield (dihydrochloride): 98%

EXAMPLE 63

2-[(4-Benzylpiperazin-1-yl)Methyl]-6-Methyl-4-Oxo [4H]-1-Benzopyran

By proceeding as in Example 2, but replacing the 2-hydroxyacetophenone in stage B by the 2-hydroxy-5-methylacetophenone, the title compound is obtained.

PHARMACOLOGICAL STUDY OF THE COMPOUNDS OF THE INVENTION

EXAMPLE A

Study of The Toxicity of The Compounds of The Invention

Protocol

The acute toxicity was assessed after the oral administration to groups of 5 mice (20±2 grams) of increasing doses (0.1–0.25– 0.50–0.75–1 g/kg) of the compounds of the invention. The animals were observed at regular intervals in the course of the first day and daily for the two weeks following treatment.

Results

It appears that the compounds of the invention are atoxic. No deaths are observed after the administration of a dose of 1 g.kg-1. No disorders are observed after the administration of that dose.

EXAMPLE B

Measurement of The Affinity of The Compounds of The Invention For σ (Sigma) Receptors Protocol The affinity of the compounds of the invention in vitro for σ receptors was determined:
by measuring the displacement of 3H-PPP ([3H]-(3 -hydroxyphenyl)-N-(1-propyl)piperidine), a specific σ receptor ligand, on preparations of the cerebral cortex of guinea pigs,
and by measuring the displacement of 3H-DTG (1,3-di-(2-tolyl)guanidine) on preparations of the brain of guinea pigs.

Results

The compounds of the invention are found to be very powerful ligands of σ (sigma) receptors with affinity constants of the order of nanomoles.

EXAMPLE C

Measurement of The Affinity of The Compounds of The Invention for $\beta_1$, $\beta_2$, $D_1$, $D_2$, $5HT_{1A}$, $5HT_{1C}$, $5HT_{1D}$, $5HT_2$ and $5HT_3$ Receptors Protocol The affinity of the compounds of the invention in vitro was determined:
in the case of $\beta_1$ adrenergic receptors, by measuring the displacement of dihydroalprenolol on preparations of the frontal cortex of rats,
in the case of $\beta_2$ adrenergic receptors, by measuring the displacement of dihydroalprenolol on preparations of the pulmonary parenchyma of rats,
in the case of $D_1$ dopaminergic receptors, by measuring the displacement of SCH 23390 on preparations of the striatum of rats,
in the case of $D_2$ dopaminergic receptors, by measuring the displacement of raclopride on preparations of the striatum of rats, in the case of $5HT_{1A}$ serotoninergic receptors, by measuring the displacement of 8-OH-DPAT (8-hydroxy-2-(di-n-propylamino)tetraline) on preparations of the hippocampus of rats, in the case of $5HT_{1C}$ serotoninergic receptors, by measuring the displacement of N-methylmesulergine on preparations of the frontal cortex and hippocampus of rats, in the case of $5HT_{1D}$ serotoninergic receptors, by measuring the displacement of 5-hydroxytryptamine on preparations of the cortex, striatum and globus pallidus of rats, in the case of $5HT_2$ serotoninergic receptors, by measuring the displacement of amino-iodoketanserine on preparations of the frontal cortex of rats, in the case of $5HT_3$ serotoninergic receptors, by measuring the displacement of BRL 43694 on preparations of the area postrema of rats.

Results

The compounds of the invention exhibit a distinctly lesser affinity for $\beta_1$, $\beta_2$, $D_1$, $D_2$, $5HT_{1A}$, $5HT_{1C}$, $5HT_{1D}$, $5HT_2$ and $5HT_3$ receptors than for $\sigma$ (sigma) receptors.

EXAMPLE D

Study of The Antagonism of Hyperactivity Induced By d-Amphetamine Sulfate in Mice Principle The aim of this test is to evaluate any antagonistic activity of the compounds of the invention on hyperactivity induced by d-amphetamine sulfate. This experiment enables the neuroleptic activity of a compound to be demonstrated.

Protocol

Male NMRI-CERJ mice are placed, one per cage, in labyrinths made up of 6 compartments (25.5×20.5×9 cm) equipped with photoelectric cells.

The number of times each animal passes between the photoelectric cells is measured for 30 minutes.

The products of the invention are tested at doses ranging from 8 to 32 mg/kg. They are injected intraperitoneally 1 hour before the start of the experiment.

The d-amphetamine sulfate (2 mg/kg) is injected intraperitoneally 30 minutes before the start of the test.

Results d-amphetamine sulfate injected only 30 minutes before the start of the experiment brings about a 113% increase in the number of movements between the photoelectric cells. From 8 mg/kg, the compounds of the invention antagonise to a significant degree the hyperactivity induced in mice by d-amphetamine sulfate, which demonstrates their neuroleptic activity.

EXAMPLE E

Study of The Antagonism of Behavioural Stereotypes Induced in Rats by Phencyclidine Principle Phencyclidine, which is a ligand of $\sigma$ (sigma) receptors, induces easily recognisable behavioural stereotypes in rats (swaying of the head, uncontrolled movements of the front paws). Conventional neuroleptics antagonise the effects of phencyclidine.

Protocol

Male WISTAR CERJ rats are injected subcutaneously with 8 mg/kg of phencyclidine and then placed, one per cage, in transparent cages (20×10×10 cm) and the intensity of the stereotypes observed is noted.

The products of the invention are injected intraperitoneally, at doses ranging from 8 to 32 mg/kg, 30 minutes before the phencyclidine.

Observations commence 10 minutes after the injection of phencyclidine and the intensity of the behavioural stereotypes is evaluated for 90 minutes.

Results

From 8 mg/kg, the compounds of the invention antagonise to a significant degree the behavioural stereotypes induced in rats by phencyclidine.

This result demonstrates the neuroleptic activity of the compounds of the invention.

EXAMPLE F

Study of The Reversal of The Effects of Apomorphine in Rats

Principle

Compounds reversing the effects of apomorphine exhibit a non-negligible activity on the extra-pyramidal system.

Using this test, it is therefore possible to establish whether or not a neuroleptic compound has any activity on the extra-pyramidal system.

This activity is expressed in effects of the Parkinsonian type, such as akinesia, trembling and rigidity of the limbs.

Protocol

The compounds of the invention are administered to male SPRAGUE-DAWLEY rats at doses varying from 1 to 16 mg/kg.

Haloperidol (1 mg/kg) injected under the same conditions is used as a reference product.

A solution of apomorphine (1 mg/kg) is injected subcutaneously 30 minutes later.

The rats are immediately placed, one animal per cage, in transparent cages and the intensity of the stereotypes observed after the administration of apomorphine is noted for 30 minutes.

Results

The compounds of the invention, even at doses of 32 mg/kg, are found to be incapable of reversing the effects induced by apomorphine in rats, while haloperidol (1 mg/kg) causes the effects to disappear completely.

This test demonstrates the absence of any activity of the compounds of the invention on the extra-pyramidal system. The compounds of the invention therefore have no secondary effects of the Parkinsonian type (akinesia, trembling and rigidity of the limbs) because they have no activity on the extra-pyramidal system.

They therefore possess pure neuroleptic and antipsychotic properties devoid of the secondary effects attributable to the extra-pyramidal component currently associated with conventional neuroleptics.

EXAMPLE G

Spontaneous Motor Activity (Activity Meter)

Protocol

Animals (rats, mice) are placed individually into plexiglass boxes equipped with photoelectric cells housed within a darkened enclosure. Six animals are tested at one time (J. R. BOISSIER et al., Arch. Int. Pharmacodyn., 158, (1965), 212– 221) and the number of interruptions by each animal of the photo-electric beams are recorded by computer at 10 minute intervals for one hour. The test compound is usually administered i.p. immediately before placing the animals in the apparatus. 12 animals are studied per dose.

Remark

In animals which have not previously been habituated to the apparatus, an increase of activity during the first half hour is suggestive of an anxiolytic effect whereas an increase in activity during the whole test reflects mainly psycho-stimulant activity. Decreases in activity generally reflect sedative activity.

Results

This test gave particularly interesting results after injection of compound of example 61. They are listed in Table I:

TABLE I

| | | Activity meter | | |
|---|---|---|---|---|
| | Number of beams crossed (Percentage change | | DOSES (mg.kg$^{-1}$ i.p.) | |
| | from control) | 16 | 32 | 44 |
| EXAMPLE 61 | 0 to 30 min. | −12% NS (0.679) | −48%* (2.753) | −71%*** (4.809) |
| | 30 to 60 min. | +7 NS (0.124) | −51% NS (1.769) | +22% NS (0.600) |

This test has been carried out on 12 mice per group.
(N.NNN)=Student's Test; NS=Not Significant; *=p<0.05 ; =p<0.01 ; *=p<0.001

EXAMPLE H

Antagonism of Amphetamine-Induced Stereotypies

Protocol

Animals are injected i.p. with d-amphetamine (8 mg.kg$^{-1}$ in mice, 4 mg.kg$^{-1}$ in rats) and are scored for the intensity of stereotypies (head movements, sniffing, licking, gnawing, repetitive body movements) on a 4 point scale. Observations are carried out every 10 minutes until the disappearance of the stereotypies. The test compound is usually administered i.p. 30 minutes before the injection of d-amphetamine. 6 animals are studied per dose (Simon P. et al., J. Pharmacol., 3, (1972), 235–238). Haloperidol (0.5 mg.kg-1 i.p.) is used as a reference compound.

Remark

Dopamine stimilant-induced stereotypies are selectively antagonized by neuroleptics, but are potentiated by a variety of agents including antidepressants, benzodiazepines, antihistamines, anticholinergics and several beta blockers.

Results

Very significants results have been obtained after injection of compound of example 61 and are listed below, in table II:

TABLE II

| | Antagonism of amphetamine-induced stereotypies | | | |
|---|---|---|---|---|
| Stereotypies (Percentage | DOSES (mg.kg$^{-1}$ i.p.) | | | Reference: Haloperidol |
| antagonism) | 8 | 16 | 32 | (0.5 mg.kg$^{-1}$) |
| Example 61 | 8% NS (0.415) | −8% NS (0.415) | 17% NS (0.674) | 100%*** (5.477) |

Test carried out on 6 mice per group.
(N.NNN)=Student's Test ; NS=Not Significant; *=p<0.05; =p<0.01 ; *=p<0.001

EXAMPLE I

D-Amphetamine-Induced Antagonism Activity on Rats

This test is based on the capacity of the compounds of the invention to inhibit induced hyperactivity on rats with 4 mg.kg-1 of amphetamine. Sprague-Dawley rats weighing from 200 to 250 g are injected i.p. with the compounds 30 minutes before administration of 4 mg.kg$^{-1}$ of amphetamine.

Rats' locomotive activity is then measured during 4 hours after administration of amphetamine.

The compounds of the invention inhibit very significatively the induced-hyperactivity of d-amphetamine, this suggesting a central-antidopaminergic activity. Results are listed in Table III:

TABLE III

| | d-amphetamine-induced antagonism activity | | | | |
|---|---|---|---|---|---|
| | | DOSES (mg.kg$^{-1}$ i.p.) | | | Reference Haloperidol |
| Compound | Activity | 8 | 16 | 32 | (0.125 mg.kg$^{-1}$) |
| Example 61 | % Antagonism | 34% NS (1.930) | 58%** (3.121) | 90%*** (5.707) | 82%*** (4.993) |
| | Intrinsic effect (% change from control) | +6% NS (0.313) | −5% NS (0.264) | −21% NS (1.173) | −9 NS (0.471) |

Test carried out on 12 mice per group.
(N.NNN)=Student's Test; NS=Not Significant; *=p<0.05; =p<0.01 ; *=p<0.001

EXAMPLE J

Pharmaceutical Composition: Tablets

Tablets each containing 5 mg of 2-[(4-benzylpiperazin-1-yl) methyl]-4-oxo[4H]-1-benzopyran Preparation formula for 1000 tablets:

| | |
|---|---|
| 2-[(4-benzylpiperazin-1-yl)methyl]-4-oxo[4H]-1-benzopyran | 5 g |
| wheat starch | 10 g |
| corn starch | 10 g |
| lactose | 65 g |
| magnesium stearate | 2 g |
| silica | 1 g |
| hydroxypropylcellulose | 2 g |

EXAMPLE K

Pharmaceutical Composition: Tablets

Tablets each containing 10 mg of 2-{[4-(2,3,4-trimethoxybenzyl)piperazin- 1-yl]methyl}-4-oxo[4H]-1-benzopyran Preparation formula for 1000 tablets:

| | |
|---|---|
| 2-{[4-(2,3,4-trimethoxybenzyl)piperazin-1-yl]methyl}-4-oxo[4H]-1-benzopyran | 10 g |
| wheat starch | 10 g |
| corn starch | 10 g |
| lactose | 65 g |
| magnesium stearate | 2 g |
| silica | 1 g |
| hydroxypropylcellulose | 2 g |

We claim:

1. A compound selected from the group consisting of 2-[(4 -benzylpiperazin-1-yl)methyl]-4-oxo[4H]-1-benzopyran, 2-{[4 -(2,3,4-trimethoxybenzyl)piperazin-1-yl]methyl}-4-oxo[4H]-1-benzopyran, 2-{[4-[(1,3-benzodioxyl-5-yl)methyl]piperazin-1-yl] methyl)-4-oxo[4H]-1-benzopyran, 2-[4-(4 -methoxybenzyl)piperazin-1-ylmethyl]-4-oxo[4H]-1-benzopyran, 2-[4-(4 -fluorobenzyl)piperazin-1-ylmethyl]-4-oxo[4H]-1-benzopyran, 2-[ (4-benzylpiperidin-1-yl)methyl]-4-oxo[4H]-1-benzopyran, 2-({[ 4-(2,4-dichlorobenzyl)piperazin-1-yl]methyl}-4-oxo[4H]-1-benzopyran, and 2-{[4-(3,4-dichlorobenzyl)piperazin-1 -yl] methyl}-4-oxo[4H]-1-benzopyran, and pharmaceutically-acceptable acid addition salts thereof.

2. A compound according to claim 1 which is selected from 2-[(4-benzylpiperazin- 1-yl)methyl]-4-oxo[4H]-1-benzopyran, and its addition salts with a pharmaceutically-acceptable acid.

3. A compound according to claim 1 which is selected from 2-([4-(2,3,4 -trimethoxybenzyl)piperazin-1-yl]methyl)-4-oxo[4H]-1-benzopyran, and its addition salts with a pharmaceutically-acceptable acid.

4. A compound according to claim 1 which is selected from 2-([4-[(1,3 -benzodioxyl-5-yl)methyl]piperazin-1-yl] methyl}-4-oxo[4H]-1-benzopyran, and its addition salts with a pharmaceutically-acceptable acid.

5. A compound according to claim 1 which is selected from 2-[4-(4 -methoxybenzyl)piperazin-1-ylmethyl]-4-oxo [4H]-1-benzopyran and its addition salts with a pharmaceutically-acceptable acid.

6. A compound according to claim 1 which is selected from 2-[4-(4 -fluorobenzyl)piperazin-1-ylmethyl]-4-oxo [4H]-1-benzopyran and its addition salts with a pharmaceutically-acceptable acid.

7. A compound according to claim 1 which is selected from 2-[(4-benzylpiperidin-1-yl)methyl]-4-oxo[4H]-1-benzopyran and its pharmaceutically-acceptable acid addition salts.

8. A compound which is selected from 2-[(4 -benzylpiperazin-1-yl)methyl]-6-methyl-4-oxo[4H]-1-benzopyran and its addition salts with a pharmaceutically-acceptable acid.

9. A pharmaceutical composition useful in the treatment of schizophrenia, which contains as active ingredient an effective amount of a compound according to claim 1 in combination with one or more pharmaceutically-acceptable excipients or vehicles.

10. A pharmaceutical composition useful in the treatment of schizophrenia, which contains as active ingredient an effective amount of a compound according to claim 8 in combination with one or more pharmaceutically-acceptable excipients or vehicles.

11. A method for treating a living animal afflicted with schizophrenia, comprising the step of administering to the said living animal an amount of a compound selected from those of formula (I):

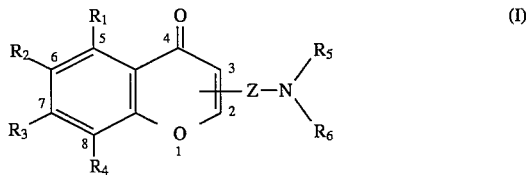

in which:

Z represents a methylene chain in ring position 2, each of
R$_1$, R$_2$, R$_3$ and R$_4$ represents hydrogen, R$_5$ and R$_6$ form together with the nitrogen atom carrying them a heterocycle selected from:
- 4-substituted piperazine, or
- 4-substituted piperidine, the term "substituted" associated with piperidine denotes that that group is substituted by a phenyl-lower-alkyl group, the term "substituted" associated with piperazine denotes that that group is substituted by one or more radicals selected from:

R$_9$, where R$_9$ represents:
- unsubstituted or substituted —(CH$_2$)$_p$-phenyl in which p is 1 to 5, inclusive, or
- unsubstituted —(CH$_2$)$_q$-naphthyl in which q is 1, and
- —(CH$_2$)$_t$-R$_{11}$, in which t is 1 and R$_{11}$ represents:
  (1,3-benzodioxol-5-yl)-lower alkyl, the term "substituted" associated with "—(CH$_2$)$_p$-phenyl" denotes that that group is substituted on the phenyl ring by 1, 2 or 3 radicals selected from:
- halogen, lower-alkyl, and lower-alkoxy, wherein lower-alkyl and lower-alkoxy have 1–6 carbon atoms, inclusive, its optical isomers, and also its pharmaceutically-acceptable acid or base addition salts, which is effective for alleviation thereof.

12. A method-of-treating according to claim 11, wherein the compound employed is selected from the group consisting of 2-[(4-benzylpiperazin-1-yl)methyl]-4-oxo[4H]-1-benzopyran, 2-{[4-(2,3,4-trimethoxybenzyl)piperazin-1-yl]methyl}-4-oxo[4H]-1-benzopyran, 2-{[4-[(1,3-benzodioxyl-5-yl)methyl]piperazin-1yl] methyl}-4-oxo[4H]-1-benzopyran, 2-[4-(4-methoxybenzyl)piperazin-1-ylmethyl]-4-oxo[4H]-1-benzopyran, 2-[4-(4-fluorobenzyl)piperazin-1-ylmethyl]-4-oxo[4H]-1-benzopyran, 2-[(4-benzylpiperidin-1-yl)methyl]-4-oxo[4H]-1-benzopyran, 2-{[4-(2,4-dichlorobenzyl)piperazin-1-yl]methyl}-4-oxo[4H]-1-benzopyran, and 2-{[4-(3,4-dichlorobenzyl)piperazin-1-yl] methyl}-4-oxo[4H]-1-benzopyran, and pharmaceutically-acceptable acid addition salts thereof.

13. A method-of-treating according to claim 11, wherein the compound employed is selected from the group consisting of 2-[4-(4-methoxybenzyl)piperazin-1-ylmethyl]-4-oxo[4H]-1-benzopyran and a pharmaceutically-acceptable acid addition salt thereof.

14. A method for treating a living animal afflicted with schizophrenia, comprising the step of administering to the said living animal an amount of a compound of claim 8 which is effective for alleviation thereof.

* * * * *

UNITED STATES PATENT AND TRADEMARK OFFICE
CERTIFICATE OF CORRECTION

PATENT NO. : 5,519,023            Page 1 of 5
DATED : May 21, 1996
INVENTOR(S) : Marc Payard, et al It is certified that error appears in the above-indentified patent and that said Letters Patent is hereby corrected as shown below:

Column 8, line 30: "(0,055 mol)" should read -- (0.055 mol) --.

Column 9, line 28 (approx.): "1-y" at end of line should read -- 1-yl] --.

Column 9, line 29: Delete "1]" at beginning of the line.

Column 9, line 33 (approx): "1-yl" at end of line should read -- 1-yl] --.

Column 9, line 34: Delete "]" at beginning of the line.

Column 9, line 39: "1-y" at end of line should read -- 1-yl] --.

Column 9, line 40: Delete "1]" at beginning of the line.

Column 9, line 60: "2-{4" at beginning of the line should read: -- 2-{[4 --.

Column 10, line 14: "1-y" at end of the line should read -- 1-yl] --.

Column 10, line 15: Delete "1]" at beginning of the line.

Column 10, line 19: "yl]methyl" should read -- yl]Methyl} --.

Column 10, line 20: Delete "}" at beginning of the line.

UNITED STATES PATENT AND TRADEMARK OFFICE
CERTIFICATE OF CORRECTION

PATENT NO. : 5,519,023
DATED : May 21, 1996
INVENTOR(S) : Marc Payard, et al

It is certified that error appears in the above-indentified patent and that said Letters Patent is hereby corrected as shown below:

Column 10, line 44 (approx): "Trimethylbenzyl)Piperazin-1-yl" should read -- Trimethoxybenzyl)Piperazin-1-yl] --.

Column 10, line 45: Delete "]" at beginning of the line.

Column 10, line 52 (approx): "Trimethylbenzyl)Piperazin-1N-1-y" should read -- Trimethoxybenzyl)Piperazin-1-yl] --.

Column 10, line 53: Delete "1]" at beginning of the line.

Column 10, line 57 (approx): "Trimethylbenzyl)" should read -- Trimethoxybenzyl) --.

Column 10, line 62: "2-{4-" should read -- 2-{[4- --.
    Pg. 17, line 4

Column 13, line 46: "DEC" should read -- Dec --; and add -- } -- to end of the line.

Column 13, line 47: Delete "}" at beginning of the line.

Column 13, line 51: "Amino]Methyl" should read -- -- Amino]Methyl} --.

Column 13, line 52: Delete "}" at beginning of the line.

UNITED STATES PATENT AND TRADEMARK OFFICE
CERTIFICATE OF CORRECTION

PATENT NO. : 5,519,023

DATED : May 21, 1996

INVENTOR(S) : Marc Payard, et al

It is certified that error appears in the above-indentified patent and that said Letters Patent is hereby corrected as shown below:

Column 15, line 3: "Trimethylbenzyl)" should read -- Trimethoxybenzyl) --.

Column 15, line 8: "3-([4-" should read -- 3-{[4- --, and "Piperazin-1-yl)" should read -- Piperazin-1-yl] --.

Column 15, line 13: "3-([4-" should read -- 3-{[4- --; and "Piperazin-1-yl)Methyl}-" should read -- Piperazin-1-yl]Methyl} --.

Column 15, line 24: "methyl]Piperazin-1-y" should read -- Methyl]Piperazin-1-yl] --.

Column 15, line 25: Delete "l]" at the beginning of the line.

Column 15, line 29: "3-([N-" should read -- 3-{[N- --.

Column 15, line 35: "(4-Methoxybezyl)" should read -- (4-Methoxybenzyl) --.

Column 18, line 13: "commenoe" should read -- commence --.

UNITED STATES PATENT AND TRADEMARK OFFICE
CERTIFICATE OF CORRECTION

PATENT NO. : 5,519,023
DATED : May 21, 1996
INVENTOR(S) : Marc Payard, et al

It is certified that error appears in the above-indentified patent and that said Letters Patent is hereby corrected as shown below:

Column 18, line 14: "phencyolidine" should read -- phencyclidine --.

Column 19, line 45 (approx): "+7NS" should read -- +7%NS --.

Column 19, line 49: "*=p<0.05" should read -- *=p<0.05;--

Column 19, line 50, Delete "," at beginning of line.

Column 19, line 54: "Stereotypies" should read -- stereotypes --.

Column 19, lines 59 and a62: "stereotypies" should read -- stereotypes --.

Column 20, line 9: "stereotypies" should read --stereotypes--.

Column 20, line 16: "significants" should read -- significant --.

UNITED STATES PATENT AND TRADEMARK OFFICE
CERTIFICATE OF CORRECTION

PATENT NO.    : 5,519,023
DATED         : May 21, 1996
INVENTOR(S)   : Marc Payard, et al It is certified that error appears in the above-indentified patent and that said Letters Patent is hereby corrected as shown below:

Column 21, line 11 (approx):   "-9NS" should read -- -9%NS --.

Column 21, line 61:   "methyl)" should read -- methyl} --.

Column 21, line 65:   "2-({[4-" should read -- 2-{[4- --.

Signed and Sealed this

Fifth Day of November, 1996

BRUCE LEHMAN

*Attest:*

*Attesting Officer*    Commissioner of Patents and Trademarks